United States Patent [19]

Blum

[11] Patent Number: 4,956,092

[45] Date of Patent: Sep. 11, 1990

[54] METHOD FOR CONCENTRATING/DEHYDRATING OF SEWAGE SLUDGE

[76] Inventor: Holger Blum, Parkallee 75, D-2000 Hamburg 13, Fed. Rep. of Germany

[21] Appl. No.: 392,366

[22] Filed: Aug. 11, 1989

[30] Foreign Application Priority Data

Aug. 23, 1988 [EP] European Pat. Off. .......... EP88 113 720.2

[51] Int. Cl.$^5$ .............................................. C02F 11/14
[52] U.S. Cl. .................................... 210/609; 210/610; 210/623; 210/631; 210/726
[58] Field of Search .............................. 210/609–611, 210/613, 614, 623, 625, 626, 631, 723, 726–729, 749, 765

[56] References Cited

U.S. PATENT DOCUMENTS

| 3,300,401 | 1/1967 | Sontheimer | 210/609 |
| 4,132,638 | 1/1979 | Carlsson | 210/609 X |
| 4,377,486 | 3/1983 | Barrick et al. | 210/609 X |
| 4,521,515 | 6/1985 | Hata | 210/611 X |

*Primary Examiner*—Tom Wyse
*Attorney, Agent, or Firm*—Birch, Stewart, Kolasch & Birch

[57] ABSTRACT

In the method for concentrating/dehydrating sewage sludge including activated sludge with the aid of organic polyelectrolytes and/or inorganic flocculators the activated sludge portion is produced in an aerated biologic clearing step in presence of—based on the amount of liquid flowing into the clearing step—5 to 0.01 parts by weight per million parts by weight of at least one compound selected from the group consisting of folic acid, dihydrofolic acid and at least an ammonium alkali metal salt, alkaline earth metal salt and alkanolammonium salt thereof.

8 Claims, No Drawings

4,956,092

METHOD FOR CONCENTRATING/DEHYDRATING OF SEWAGE SLUDGE

BACKGROUND OF THE INVENTION

The invention relates to a new method for concentrating and dehydrating sewage sludge including activated sludge of an aerated biologic clearing step.

The aim to be achieved by the methods in industrial and/or local bio-aerobic sewage clarification is the production of an easily filtrable, compact sewage sludge having a high amount of dry substance contents in the filter cake. The reduction of the volume of sludge accompanying a high amount of dry substance contents by separating off the water portion permits a cost-effective and energy-saving further treatment of the sewage sludge by storing it on dumping grounds, burning it or using it in agriculture.

Sewage sludge consists of the so-called primary sludge obtained in the preliminary sedimentation by precipitation in presence of organic and/or inorganic flocculators and of the activated sludge produced in the biologic clearing step. Depending on the type and operating mode of the sewage treatment plant the sewage sludge contains between about 10 % to 90 % by weight of activated sludge. While the primary sludge corresponding to its origin by precipitation in the preliminary sedimentation basin generally shows good filterability properties (dry substance contents and filtration velocity), mixtures out of primary sludge and activated sludge as a rule are difficult to concentrate and dehydrate.

According to the state of art a so-called flocculation aid is added to the activated sludge, the so-called excess sludge, originating from the biologic clarifications step in the secondary sedimentation basin for improving the sedimentation and dehydration behaviour. The thus pretreated excess sludge is mixed with the primary sludge in the secondary concentrator and the sludge mixture is dehydrated in centrifuges, band filter presses or chamber filter presses.

The adding of flocculation aids can also be effected in another step, e.g. in the so-called secondary concentration—dosed into the mixture of primary and excess sludge—instead of being effected in the secondary sedimentation basin. The filter or centrifuge cake of the sewage sludge always contains more or less large portions of organic and/or inorganic flocculation aids apart from primary and activated sludge. The composition and the way of use of flocculation aids is known to the expert. In a largely used method the sludge to be filtered is treated with iron(III)salt, e.g. iron(III)-chloride and calcium hydroxide, in such manner that about 20 to 60 kgs of iron(III)chloride and 75 to 180 kgs of calcium hydroxide per ton of dry solid substance are used. By this way of action a compact, easily filterable sewage sludge is obained which, however, is loaded with additional amounts of slag-forming inorganic substances.

According to this so-called iron-lime method preferably organic polymeric flocculators are used for concentration/dehydration of sewage sludge including activated sludge. Polymeric flocculators are water-soluble, chain-forming polymerizates mostly produced by polymerization of acrylamide (e.g. as defined in the German publication 2,025,725 or 2,337,337 or Japan Kokai 75/161,479 or Japan Kokai 75/53,274 or Japan Kokai No. 74/59,855). It is, however, also possible to condense other polymerizable monomers, e.g. ethylene oxide (USSR Patent No. 1,204,576), ethyleneimine, allyl guanidines (U.S. Pat. No. 3,878,170) or quarternary carboxylic acid esters (Japan Kokai No. 76/04,084) or polyamines (U.S. Pat. No. 3,174,928, Spanish Patent No. 287,939, Japan Kokai Tokio Koho No. 86/192,734) to polyelectrolytes in chain form. In dependance on their electrostatic charge in aqueous solution a distinction is made between nonionnic, anion-active and cation-active polymeric flocculators. The combination, too, of inorganic/organic agents, such as pulverized brown coal plus polymers, is known for use as flocculator to the expert.

Per ton of solid substance about 1 kilogram to 7 kilograms of polymeric polyelectrolyte are required for achieving a sufficiently fast concentration and dehydration of the sewage sludge. By the use of organic polyelectrolytes the problem of the large amount of slag-forming inorganic substances in the filter cake of the sewage sludge (iron-lime method) is solved, however, the organic flocculators used instead represent a substantial cost factor which can decisively reduce the economy of sludge concentration and dehydration.

Therefore, numerous attempts have been made to modify the operation mode of sludge concentration and dehydration by means of the above-named organic polymeric flocculators in such manner that the required amount used is reduced to a minimum.

Japanese patent specification Kokai Tokio Koho No. 79/113,954, e.g., teaches the use of cation-active non-ionic copolymers of definite molar conditions for increasing the efficiency in the dehydration of sludges. European patent application 159,178 as well as Japan Kokai Tokio Koho No. 87/102,892 teach the use of synergistically acting inorganic/organic flocculating/charging agents for the purpose of saving polymers. In the patent specification Japan Kokai No. 75/141,850 a method is described for concentrating/dehydrating sewage sludges with reduced polymer consumption, in which method the sludge primarily is treated with a part of the sedimented clarifying agent of a previous precipitation, whereupon concentration of the pretreated sludge is effected using a reduced amount of fresh polymer. Japan Kokai No. 75/86,476 describes a synergetically acting combination of aluminium salts and non-ionic polyacrylamide for sludge dehydration.

The above-described synergetic methods require an accurate survey of the properties of the sludge to be dehydrated as well as a continuous checking of the precipitation/dehydration process for being able to make use of the advantages cited in the patent specifications. Japan Kokai Koho No. 87/132,600 describes, e.g., the analytic expenditure for predicting the dehydration behaviour of the sewage sludge. With the large variations of the flocculation and dehydration behaviour of mixed sludge ocurring in local and industrial sewage sludge treatment the use of the above-mentioned synergetic methods is limited.

It is, therefore, the object of the present invention to find a method for concentrating/dehydrating sewage sludge, which method permits a real reduction of the required amount of organic and/or inorganic flocculation agents independently from variations in the flocculation and dehydration behaviour of sewage sludge comprising activated sludge.

It has been found that said problem can be solved in accordance with the present invention in that the activated sludge portion of the sewage sludge to be dehydrated is produced in an aerated biologic clarification step in the presence of at least one compound selected from the group consisting of folic acid, dihydrofolic acid and at least one salt thereof.

SUMMARY OF THE INVENTION

The present invention relates to a method for concentrating/ dehydrating sewage sludge including activated sludge in presence of organic polyelectrolytes and/or inorganic flocculators, which comprises producting the activated sludge portion in an aerated biologic clarification step in presence of at least one compound selected from the group consisting of folic acid, dihydrofolic acid and at least one salt thereof.

DETAILED DESCRIPTION OF THE INVENTION

The procedural method according to the present invention independently from variations in the composition and the dehydration behaviour of the primary sludge permits a simultaneous operation of the sludge concentration and filtration/ centrifugation and requires only minimal efforts for analytically surveying the procedural steps. Furthermore, the procedural method according to the present invention permits, contrary to hitherto known methods, to effect a significant reduction of flocculators without new substances detrimental for the environment being introduced into the circulation of industrial or local sewage water purification.

The folic acid and/or dihydrofolic acid and/or the salts thereof are added in amounts of 5 to 1.1 ppm, preferably 1 to 0.01 ppm, based on the sewage water flowing into the biologic clarification step.

According to a preferred embodiment of the present invention continuously about 1 to 0.01 ppm of folic acid and/or dihydrofolic acid and/or at least one ammonium alkali metal salt, alkaline earth metal salt and/or alkanolammonium salt thereof are dosingly added to the prepurified sewage water flowing into the biologic clarification step.

In another preferred embodiment of the procedural method according to the present invention continuously 1 to 0.01 ppm, based on the prepurified sewage water flowing into the clarification step, of folic acid and/or dihydrofolic acid and/or at least one ammonium alkali metal salt, alkaline earth-metal salt and/or alkanolammonium salt thereof is dosingly added into the so-called sludge back flow. After some days the amount of flocculators priorily having been required in the sewage sludge concentration/dehydration can be reduced step by step without worsening of the sedimentation and dehydration behaviour of the sewage sludge.

If the inventive method is carried out by dosingly adding aqueous alkali or alkaline earth metal salt solutions or alkanolammonium salts of folic acid

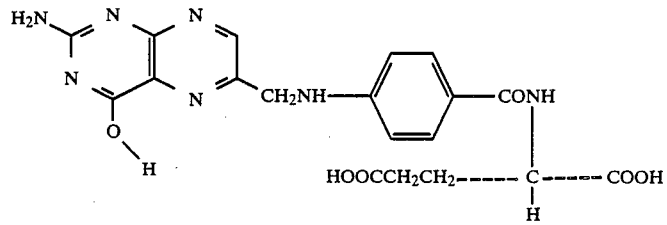

to the activated sludge in the aerobic biologic clarification step and in dehydrating the thus treated excess sludge alone or mixed with primary sludge, due to the insufficient stability of the folic acid in aqueous solution a concentration of about 0.5 to 3 ppm of folic acid with respect to the sewage water flowing into the activated basin is required for achieving the desired improvement effect in dehydration of the sewage sludge.

If in contrast thereto, as can be seen from the Belgian patent specification No. 88.00333, instead of pure folic acid its derivative dihydrofolic acid

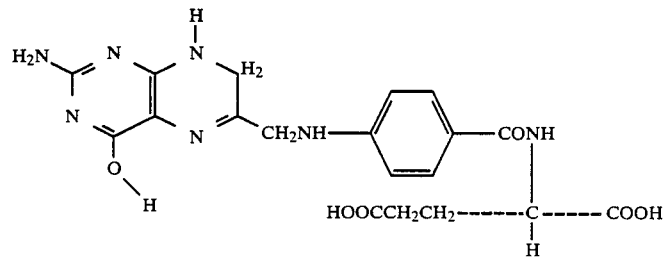

and/or mixtures of folic acid and dihydrofolic acid are dosingly added to the activated sludge in form of the alkali or alkaline earth metal salt solutions or alkanolammonium salt solutions, so due to the good stability of the folic acid/dihydrofolic acid solution in aqueous solution only concentrations of about 0.01 to 0.1 ppm of folic acid/dihydrofolic acid mixture, based on the sewage water flowing into the activated basin, are required for achieving the desired improvement effect in dehydrating the sewage sludge.

Stable folic acid preparations are described in EP-87 118 082.4. The term "alkali metal salts" used herein is intended to mean the lithium, sodium, potassium, rubidium and caesium salts.

The term "alkaline earth metal salts" used herein is intended to mean the magnesium, calcium, strontium and barium salts.

Under the above-mentioned expression "ammonium salts" ammonium salts as well as also tetraalkylammonium salts, with the cation $NH_4^+$ or $NR_4^+$, respectively, are to be understood, wherein R is an alkyl residue with preferably 1 to 6, in particular 1 to 4, especially 1 to 3 carbon atoms.

The ammonium salt preferably is a salt of the above-named organic acids with a dialkanolamine of the formula

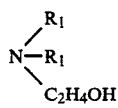

wherein, R1 is hydrogen and/or hydroxyethyl and/or hydroxypropyl.

One feature of the method according to the present invention lies in the fact that the effect of improved sludge dehydration will occur with a temporal delay only. Generally 5 to 10 days of first runnings upon adding of folic acid/dihydrofolic acid solution are required before the effect will take place. If the adding process is interrupted, the effect may still be observed for several days.

In spite of the fact that it is known that folic acid hardly is present in sewage treatment plants and stimulates the growth of various microorganisms (H. Mohr; Folic Acid - Micronutrient and Growthpromotor for Bakteria and Fungi. An Outline, BioTechnologie 10, 1987) it could not have been expected that such an synergistic effect would occur with usual flocculators upon addition of the above-mentioned folic acid and/or dihydrofolic acid and/or the salts thereof to the biologic aerobe clarification step in the dehydration of mixed sludge.

The procedural method according to the present invention will be explained in more detail using the following examples without being restricted thereto.

DETAILED ACCOUNT OF EXAMPLES OF THE INVENTION

EXAMPLE 1

In a local sewage treatment plant a mixture of 30 to 40 % by weight of activated sludge and 70 to 60 % by weight of primary sludge were treated in a chamber filter press plant. In order to increase its fiterability, the mixed sludge being in the detention container before the filter press contained about 4 % by weight of iron(III)-chloride and 8 % by weight of calcium hydroxide, based on the sludge dry substance. With this amount of flocculators a filter output between 26 and 40 kilograms/m$^2$/bar/hour was achieved. The contents of dry substance sewage sludge in the filter cake was about 26/28 % by weight. This procedural method and the operating parameters have proved to be constant and optimal during a period of time of 6 months prior to a change to the procedural method of the present invention.

For the purpose of changing to the procedural method according to the present invention a 0.5-% solution of the disodium salt of the folic acid in distilled water was dosingly added into the inlet to the activated basin by means of a dropping means. Every day about 2500 cbm of sewage water from the preliminary sedimentation flew through the activated basin. The sludge concentration in the activated basin was from 2 to 4 grams of dry substance per liter, and the chemical oxygen demand in the preliminary sedimentation basin was from 700 to 1100 mg per liter. These operating values corresponded to those of the prior period. The dosing means for the aqueous folic acid solution was set such that 1.1 grams of sodium folat were dosingly added to each cubic meter of presedimented sewage water flowing into the activated basin (= folic acid concentration or 1 ppm).

Ten days after the beginning of the folat addition the filter output had increased to 50 to 60 kilograms/m$^2$/bar/hour. The iron/lime amount thereupon was reduced to about 3 % by weight of iron(III)chloride and 4 % by weight of calcium hydroxide based on the sludge dry substance, no decrease of the filter output taking place. Upon ten further days of folat dosing the iron/lime amount could be reduced to about 2 % by weight of iron(III)chloride and 3 % by weight of calcium hydroxide, based on the sludge dry substance, the filter output remaining constant at 50 to 60 kilograms/m$_2$/bar /hour.

After 40 days the folat dosing was interrupted, thereafter the good filter output being maintained up to the 48th day and then decreasing visibly. After 60 days again an amount of flocculator of about 4 % by weight of iron(III)chloride and 8 % by weight of calcium hydroxide, based on the sludge dry substance, was required for achieving a sufficient filter output.

EXAMPLE 2 (COMPARATIVE EXAMPLE)

The test of example 1 was repeated in the same sewage treatment plant, in dosingly adding 0.11 grams of sodium folat dissolved in one liter of water to each cubic meter of presedimented sewage water flowing into the activated basin. (= folic acid concentration of 0.1 ppm). An improved filter output and thus a reduction of the iron/lime amount was not achieved.

EXAMPLE 3

In a mineral oil refining plant a load per day with a biological oxygen demand of 2000 kg BOD5/d (BOD5-=biological oxygen demand in 5 days) was degraded by means of four activated basins in serial connection. The activated sludge arrived in a secondary sedimentation basin where the excess sludge was drained off and conveyed to a sludge detention basin. The excess sludge was dehydrated in three structurally identical chamber filter presses with the aid of 20 kilograms of lime hydrate and 8 kilograms of iron(III)chloride per cubic meter of filter cake from the filter press for obtaining a disposable filter cake with about 35 % of solid substance contents.

For the purpose of changing to the procedural method according to the present invention 0.23 grams of technical grade 90 % calcium dihydrofolate dihydrate—predissolved in 1 kilogram of distilled water—was dosingly added to each cubic meter of sewage water flowing into the second of the activated basins arranged in series ( folic acid concentration of 0.018 ppm, dihydrofolic acid concentration =0.18 ppm). After 30 days of operation on basis of the procedural method according to the present invention the filtration speed for the sewage sludge (activated sludge portion 70 % by weight) had increased such that at a solid substance concentration remaining constant instead of three only two of the present chamber filter presses were still required for dehydrating the incoming sludge load. Simultaneously the demand of flocculators could be reduced to 10 kilograms of lime hydrate and 4 kilograms of iron(III)chloride per cubic meter of filter cake.

EXAMPLE 4

In accordance with the Belgian patent specification 88.00333, example 12, an aqueous solution of folic acid, dihydrofolic acid and citric acid was produced using sodium hydroxide solution and potassium hydroxide solution. The pH value of the solution was 10.4. 100 grams of the solution contained 8 mmol of folic acid salt, 8 mmol of dihydrofolic acid salt and 5 mmol of citric acid salt.

The above folic acid/dihydrofolic acid preparation was - upon having been further diluted with tap water in a ratio of 1:100 parts by volume—dosingly added into the activated sludge back flow line of the aerated clarification step of a local sewage water administration union. The sewage treatment plant did not include a digestion tower, and the dehydration of the sewage sludge was effected with the aid of a high-molecular, water soluble, cationic polymer on basis of acrylic acid esters. Every day 60,000 cubic meters of sewage water were introduced from the presedimentation basin into the four parallel activated sludge basins equipped with dip tube aeration. It was taken account of the fact that a part of the dosingly added folic acid/dihydrofolic acid preparation was lost, because only 70 % of the back-flow sludge was transported back into the activated basins. Thus an effective dosis concentration of 0.01 ppm of folic acid and 0.01 ppm of dihydrofolic acid in the sewage water flowing into each of the parallel activated basins was the result.

After 15 days of operation with the procedural method according to the present invention—maintaining the continuous amount of folate dosing—the amount of cationic polymer used in dehydration of the sewage sludge could be reduced to 30 % of the value required prior to the use of the folic acid/dihydrofolic acid preparation.

What is Claimed

1. A method for concentrating/dehydrating sewage sludge including activated sludge in the presence of organic polyelectrolytes and/or inorganic flocculators, which comprises producing the activated sludge portion in an aerated biologic clarification step in the presence of at least one compound selected from the group consisting of folic acid, dihydrofolic acid and at least one salt thereof.

2. The method as defined in claim 1, which comprises producing the activated sludge portion in the presence of 5 to 0.01 parts by weight per million parts by weight (ppm), based on the amount of liquid flowing into the biologic clarification step, of the said at least one compound.

3. The method as defined in claim 2, which comprises producing the activated sludge portion in the presence of 1 to 0.01 parts by weight per million parts by weight (ppm), based on the amount of liquid blowing into the biologic clarification step, of the said at least one compound.

4. The method as defined in claim 1, wherein the said at least one compound is continuously dosingly added to presedimented sewage water flowing into the biologic clarification step.

5. The method as defined in claim 1, wherein the said at least one compound is continuously dosingly added to sludge back flow.

6. The method as defined in claim 1, wherein the at least one salt of the said compound is an alkali metal salt, alkaline earth metal salt, ammonium salt and/or alkanolammonium salt.

7. The method as defined in claim 6, wherein the at least one salt is the sodium, potassium, calcium or hydroxyethyl ammonium salt of the said compound.

8. The method as defined in claim 1, wherein the said compound is added in an aqueous solution.

* * * * *